United States Patent [19]

Immel et al.

[11] 4,122,290
[45] Oct. 24, 1978

[54] PROCESS FOR THE PREPARATION OF TRIMETHYLOLALKANES

[75] Inventors: Otto Immel; Hans-Helmut Schwarz; Oskar Weissel; Heinrich Krimm, all of Krefeld, Germany

[73] Assignee: Bayer Aktiengesellschaft, Leverkusen, Germany

[21] Appl. No.: 861,472

[22] Filed: Dec. 16, 1977

[30] Foreign Application Priority Data

Jan. 22, 1977 [DE] Fed. Rep. of Germany ....... 2702582

[51] Int. Cl.² .............................................. C07C 29/14
[52] U.S. Cl. ...................................... 568/853; 260/602
[58] Field of Search ........................ 260/635 A, 635 P

[56] References Cited

U.S. PATENT DOCUMENTS

| | | | |
|---|---|---|---|
| 2,206,379 | 7/1940 | Wyler | 260/635 P |
| 2,240,735 | 5/1941 | Wyler | 260/635 P |
| 2,400,724 | 5/1946 | Walker | 260/635 A |
| 3,504,042 | 3/1970 | Shimono et al. | 260/635 P |

FOREIGN PATENT DOCUMENTS

| | | | |
|---|---|---|---|
| 1,048,567 | 1/1959 | Fed. Rep. of Germany | 260/635 P |
| 2,431,814 | 1/1974 | Fed. Rep. of Germany | 260/635 P |

OTHER PUBLICATIONS

Ogata et al., "J. Chem. Soc.", No. 10, 1967, pp. 1013-1020.

*Primary Examiner*—Joseph E. Evans

*Attorney, Agent, or Firm*—Burgess, Dinklage & Sprung

[57] ABSTRACT

An improved process for the preparation of a trimethylolalkane of the formula

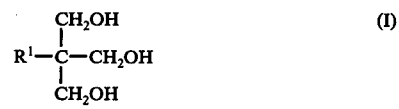

(I)

wherein
$R^1$ denotes an aliphatic radical by reacting formaldehyde with an aldehyde of the formula

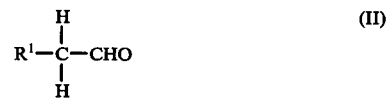

(II)

wherein
$R^1$ has the meaning indicated above and thereafter hydrogenating the resultant 2,2-dimethylolalkanal, the improvement residing in employing formaldehyde in a molar ratio of at least 8:1 to the aldehyde reactant, carrying out the aldehyde-formaldehyde reaction in the presence of an aldol condensation base at a temperature between −20 and 5° C, optionally in the presence of an ion of an element of group VII and/or VIII and/or sub-group I or II of the periodic system.

7 Claims, No Drawings

PROCESS FOR THE PREPARATION OF TRIMETHYLOLALKANES

BACKGROUND OF THE INVENTION

1. Field of the Invention

The invention relates to a process for the preparation of trimethylolalkanes by reacting alkanals with formaldehyde in the presence of a basic condensing agent and subsequently hydrogenating the resulting 2,2-dimethylolalkanal.

It is known, from German Auslegeschrift No. 1,154,080, to prepare trimethylolpropane by an alkaline condensation reaction of formaldehyde and butyraldehyde. The reaction can be represented by the following equation:

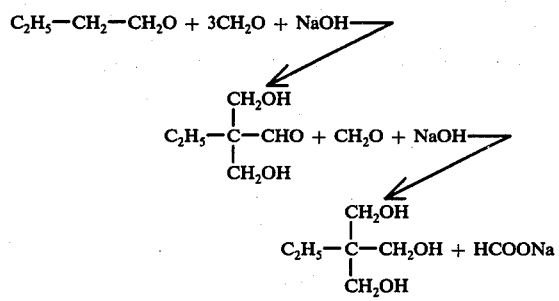

In this process, 2,2-dimethylolbutanal is transiently formed as an intermediate product and reacts with formaldehyde and the base by the Cannizzaro reaction to give trimethylolpropane and the formate.

In the industrial preparation of trimethylolpropane at least stoichiometric amounts of sodium formate are thus necessarily obtained as a by-product. The sodium formate can indeed also be fed to an appropriate utilisation process, but the demand for sodium formate is not as great as that for trimethylolpropane. The sodium formate unavoidably obtained thus results in considerable problems of disposal and environmental protection. which could hitherto only be solved in an economical manner only by dumping. It has therefore already been proposed in German Offenlegungsschrift No. 2,507,461 to initially prepare the dimethylolalkanal in a first stage, and thereafter hydrogenate it to the trimethylolalkane in the customary manner.

It has now been found that a trimethylolalkane of the formula

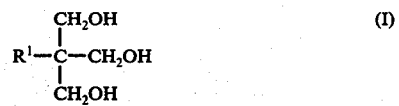

in which

R$^1$ denotes an aliphatic radical, is obtained in a simple manner and with a good yield by reacting an aldehyde of the formula

in which

R$^1$ has the meaning indicated above, with formaldehyde in a molar ratio of at least 1:8 in the presence of a base and at a temperature of from $-20°$ to $5°$ C., optionally in the presence of ions of an element of group VII and/or VIII and/or sub-group I and/or II of the periodic table of the elements, and hydrogenating the resultant 2,2-dimethylolalkanal in the customary manner.

Surprisingly, the process according to the invention permits use of bases which are in themselves customary and known for the aldo condensation while obtaining the factory yields of the dimethylolalkanal previously obtained only in accordance with German Offenlegungsschrift No. 2,507,461. employing a tertiary aliphatic amine in which at least one alkyl radical is highly branched, in particular neopentyl-N-dialkylamines, for example dimethylaminoneopentanol, as base.

The reaction according to the invention is preferably carried out in the temperature range between about $-5°$ C. and $0°$ C.

Cotemplated aliphatic radicals are optionally substituted, straight-chain or branched alkyl radicals with up to 12, in particular 1 to 6, carbon atoms contemplated substituents of these radicals are groups which are inert under the reaction conditions, in particular alkyl groups or alkoxy groups with 1 to 3 carbon atoms in each case. Examples of aldehydes of the formula II which may be mentioned are: 3-ethyl-, 3-n-propyl-, 3-isopropyl-, 3-n-butyl-, 3-isobutyl-, 3-sec.-butyl- and 3-tert.-butyl-butanal and corresponding -n-pentanals, -n-hexanals and -n-heptanals; 4-ethyl-, 4-n-propyl-, 4-isopropyl-, 4-n-butyl-, 4-isobutyl-, 4-sec.-butyl- and 4-tert.-butyl-pentanals, -n-hexanals and -n-heptanals; 5-ethyl-, 5-n-propyl-, 5-isopropyl-, 5-n-butyl-, 5-isobutyl-, 5-sec.-butyl- and 5-tert.-butyl-n-hexanals and -n-heptanals; 3-methyl-hexanal and 3-methyl-heptanal; 4-methyl-pentanal, 4-methyl-heptanal, 5-methyl-hexanal and 5-methylheptanal; and 3,3,5-trimethyl-n-pentyl-, 3,3-diethylpentyl-, 4,4-diethylpentyl-, 3,3-dimethyl-n-butyl-, 3,3-dimethyl-n-pentyl-, 5,5-dimethylheptyl-, 3,3-dimethylheptyl-, 3,3,4-trimethylpentyl-, 3,4-dimethylheptyl-, 3,5-dimethylheptyl-, 4,4-dimethylheptyl-, 3,3-diethylhexyl-, 4,4-dimethylhexyl-, 4,5-dimethylhexyl-, 3,4-dimethylhexyl-, 3,5-dimethylhexyl-, 3,3-dimethylhexyl-, 3,4-diethylhexyl-, 3-methyl-4-ethylpentyl-, 3-methyl-4-ethylhexyl-, 3,3,4-trimethylpentyl-, 3,4,4-trimethylpentyl-, 3,3,4-trimethylhexyl-, 3,4,4-trimethylhexyl- and 3,3,4,4-tetramethylpentyl-aldehyde; propanal, n-butanal, n-pentanal, 3-methylbutanal, n-hexanal, 3-methylpentanal, n-heptanal, 4-methylhexanal and n-octanal are preferred.

The process according to the invention is illustrated by the equation which follows, using butyraldehyde as an example.

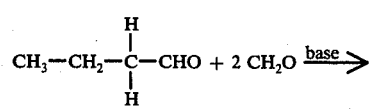

-continued

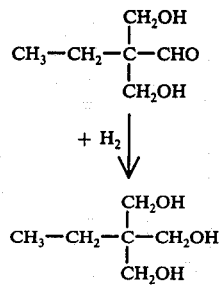

In the first reaction stage, the aldehyde of the formula II is reacted with formaldehyde in a molar ratio of at least 1:8, preferably in a molar ratio of 1:8 to 1:30, in the presence of a base, in the temperature range, according to the invention, indicated above.

In general, formaldehyde is employed as an aqueous solution, preferably containing 20 to 40% by weight of formaldehyde, appropriately in a commercially available concentration, e.g. formalin. Useful bases include the bases which are known and customarily used for the aldol condensation. Examples which may be mentioned are hydroxides and carbonates of alkali metals and alkaline earth metals, and tertiary amines. Mixtures of these bases can also be used.

Tertiary amines which can be used are heterocyclic, cycloaliphatic and, preferably, aliphatic tertiary amines, for example trimethylamine, tri-n-propylamine, tri-isopropylamine, tri-n-butylamine, triisobutylamine and tri-tert.-butylamine, and also unsymmetrical trialalkylamines, such as methyldiisopropylamine or dimethyl-tert.-butylamine; diamines, such as N,N-tetramethyl-ethylenediamine; N,N-dimethylcyclohexylamine; N-methyl-pyrrolidine, N-methyl-piperidine and N-methyl-morpholine; and amines substituted by further functional groups, such as N,N-dimethylaminoethanol.

Moreover, araliphatic amines, such as tribenzylamine, and polyamines with secondary and primary amino groups, such as triethylenediamine and tetra-methylenediamine, are also possible. Tetraalkylammonium hydroxides can also be employed as bases.

In general, bases are used in the process according to the invention in an amount of 0.01 to 0.3 mol per mol of aldehyde of the formula II. The pH value of the reaction solution is preferably from 9 to 12, more preferably 11 to 12.

When carrying out the first stage of the process according to the invention, it can be advantageous to add organic solvents to the mixture of the aldehyde of the formula II and to the aqueous formaldehyde in order to achieve a better solubility of the aldehyde of the formula II in the aqueous formaldehyde solution or to achieve a homogeneous solution.

Such organic solvents which can be used are the solvents which are known for this purpose, preferably lower aliphatic alcohols, such as methanol, ethanol, propanol and isopropanol; and alicyclic ethers, such as tetrahydrofurane and dioxane.

The amount of solvent which is appropriately used depends on the nature of the aldehyde of the formula II and can appropriately be easily determined by some preliminary experiments.

The first stage of the process according to the invention can be carried out either discontinuously or continuously. In the case of a discontinuous procedure, for example, the aldehyde of the formula II, the formaldehyde solution and the base, in the chosen ratio, and optionally the organic solvent, can be added together at the chosen temperature, whilst stirring, and the reaction mixture kept at the reaction temperature for an appropriate time.

In general, reaction times between 2 and 24 hours, in particular 5 to 12 hours, are necessary for carrying out the aldol condensation, that is to say the first reaction stage. The reaction time required in an individual case can be easily determined in the customary manner by following the course of the reaction using analytical methods, or by a few preliminary experiments.

In general, this first stage of the process according to the invention is carried out under normal pressure. However, one can also carry out the reaction under reduced pressure or under elevated pressure.

In a particular embodiment of the process according to the invention, the first stage of the process, namely the aldol condensation, is carried out in the presence of ions of an element of group VII and/or VIII and/or sub-group I and/or II of the periodic system of the elements, preferably of the elements cobalt, nickel, copper, manganese, zinc, silver and/or cadmium.

These ions are appropriately added to the reaction mixture in the form of water-soluble salts in an amount of 0.001 to 0.03, preferably 0.002 to 0.01 mol, per mol of the aldehyde of the formula II. In this procedure, the type of anion is unimportant.

The 2,2-dimethylolalkanal obtained as the reaction product of the first stage of the process according to the invention is subsequently reduced in the customary manner to the trimethylolpropane of the formula I. In this procedure it is not necessary to isolate the 2,2-dimethylolalkanal before the reduction. However, some or all of the excess formaldehyde and the solvent optionally used are advantageously separated off before the reduction. This can be effected, for example, by distillation, preferably under pressure, or by stripping process known from German Offenlegungsschrift No. 2,507,461.

In the second stage of the process according to the invention, the reduction of the resulting 2,2-dimethylolalkanal to the end product, that is to say the trimethylolalkane, is effected in a manner which is in itself known. It can be carried out either with catalytically activated hydrogen or with nascent hydrogen. Furthermore, the 2,2-dimethylolalkanal can also be reduced with alkylaminoboranes and/or borohydrides of the alkali metals and alkaline earth metals.

The 2,2-dimethylolalkanal obtained in the first stage of the process according to the invention is preferably hydrogenated in the presence of a hydrogenation catalyst under an elevated hydrogen pressure.

As already mentioned, the reaction mixture of the first stage can be fed to the catalytic hydrogenation either without further pre-treatment or after separating off low-boiling constituents, but it can be advantageous to recover the amine used as the base and the formaldehyde employed in excess. For example, the reaction mixture obtained in the first stage can be partially distilled, for example in the pressure range between 0.5 and 8 bars, in order to recover at least some of the excess formaldehyde and optionally some of the amine.

Furthermore, it can be appropriate to adjust the pH value of the reaction mixture obtained in the first stage to the most favourable value for the hydrogenation, before the hydrogenation, by adding acid in the customary manner.

If all or some of the excess formaldehyde, if appropriate the solvent and the amine have been removed, it can furthermore be appropriate to dilute the evaporation or distillation residue with water or another customary solvent, for example dioxane or isopropanol, before the hydrogenation.

In general, the hydrogenation is carried out in the temperature range between room temperature (about 20° C.) and 200° C., preferably from about 50° to 170° C., in particular between 80° and 130° C. In this procedure, the hydrogen pressure can be 1 to 500 bars, preferably 50 to 400 bars, in particular 100 to 300 bars.

Hydrogenation catalysts which can be used are those which contain, as the catalytically active constituent, an element of group 8 and/or of sub-group 1 of the periodic system, that is to say one of the elements iron, cobalt, nickel, ruthenium, rhodium, palladium, osmium, iridium, platinum and/or copper, silver or gold.

Platinum, ruthenium, cobalt, nickel and copper may be mentioned as prefered catalysts.

These catalysts can be used in the form of skeleton catalysts, supported catalysts or mixed catalysts.

Mixed catalysts based on nickel and cobalt are preferably used, in particular those which contain chromium, aluminium, magnesium, barium, zinc, manganese, thorium and/or copper as further constituents, for example nickel chromite catalysts having the composition Ni-Cr-Al-Cu, Ni-Cr-Zn-Ba or Ni-Cr-Mg-Th-Ba-Cu, or cobalt catalysts having the composition Co-Mg-Cu or Co-Mn-Cu.

The hydrogenation can be carried out in the customary manner, either discontinuously or continuously, for example in stirred autoclaves or in a reaction tube. The customary arrangements of apparatus of the most diverse nature are suitable for carrying out the hydrogenation. One can, for example, carry out the hydrogenation as a sump phase process or as a trickle phase process.

In the discontinuous procedure, the hydrogenation is preferably carried out in the customary manner as a sump phase process in an autoclave in the presence of pulverulent catalysts.

The hydrogenation can be particularly advantageously carried out continuously. In this procedure, the process can be carried out in the customary way using, a pulverulent catalyst, for example in accordance with the bubble column principle, in a manner such that the liquid starting material, in which the catalyst is suspended, is passed, together with hydrogen in co-current, through a reactor cascade, or using a catalyst in the form of lumps, for example in accordance with the trickle phase principle, in a manner such that the starting material trickles, in the liquid form, over the stationary catalyst, which is in the reaction tube, whilst the hydrogen is passed through the reaction tube in cocurrent or counter-current. In this procedure, excess hydrogen can advantageously be recycled.

After the hydrogenation has ended, the working up is carried out in the customary manner. If necessary the hydrogenation catalyst is first separated off, for example by filtration. The separation of the trimethylolalkane obtained as the reaction product can also be carried out in the customary manner, for example by distillation under reduced pressure. It can be appropriate here to carry out the distillation in two or more stages. In a first stage, the mixture obtained after the hydrogenation is distilled under pressures of, for example, 40 to 70 mm Hg, the low-boiling compounds, such as methanol, which is formed by the hydrogenation of any formaldehyde which may still be present, and any amine which may still be present and, if appropriate, organic solvent from the first reaction stage, being separated off. In a further distillation stage, the resulting trimethylolalkane is then distilled under reduced pressure, for example between 0.1 and 5 mm Hg, it being possible for it to be taken off as the top product, for example at 160° to 170° C. in the case of trimethylolpropane.

The trimethylolalkanes of the formula I which can be obtained by the process according to the invention, in particular trimethylolpropane, are intermediate products which are important industrially for the preparation of plasticizers, lacquer raw materials, polyesters and polyurethanes (Ullmann's Encyklopadie der techn. Chem., 4, Aufl., Band 7, p. 231 and p. 234 (1974)).

The technical advance of the process according to the invention, in particular for the preparation of trimethylolpropane, is based on the following. According to the process of German Offenlegungsschrift No. 2,507,461 it was indeed possible, according to the state of the art, by means of the two-stage preparation of the trimethylolalkanes, to avoid an undesired automatic production of formate, but the reaction of the aldehyde of the formula II with formaldehyde required the presence of amines which are not readily accessible in order to achieve satisfactory yields. By the process according to the invention, even better yields are now achieved from the condensation in the presence of customary bases.

This surprising advance is due to the use of a large excess of formaldehyde and of low temperatures. It was not foreseeable since, according to the state of the art, elevated temperatures have always been used in order to accelerate the reaction and the excess of formaldehyde has always been kept low in order to avoid side reactions.

EXAMPLE 1

1,000 g of aqueous formaldehyde solution (about 30% by weight formaldehyde, 10 mols) were cooled to 0° C. and 25 g of 20% strength by weight sodium hydroxide solution (0.12 mol) and 25 ml (0.18 mol) of triethylamine were added. 72 g (1.0 mol) of n-butanal were added dropwise to this mixture in the course of 15 minutes, whilst maintaining a temperature of about 0° C. and whilst stirring. The reaction mixture was then left to stand for a further 45 hours at temperatures between about −4° C. and about 0° C. Thereafter, it was neutralised with acetic acid, and 100 g of the solution were hydrogenated in an autoclave in the presence of 15 g of a Ni-Cr-Al catalyst at about 110° C. and under a hydrogen pressure of 200 to 280 bars.

The analysis of the hydrogenation mixture gave, when converted, a yield of 88.5% of theory of trimethylolpropane, relative to the n-butanal employed.

EXAMPLE 2

1 g (0.005 mol) of copper acetate was dissolved in 1,000 g of an aqueous formaldehyde solution (about 30% by weight of formaldehyde). The solution was cooled to about 0° C. and first 25 g of 20% strength by weight sodium hydroxide solution and then 72 g of n-butanal were added dropwise at this temperature, whilst stirring. The reaction mixture was then left to stand for 41 hours at temperatures of about −4° C. to about 0° C. and thereafter was neutralised with acetic acid.

100 g of this solution were then hydrogenated in the presence of 15 of a Ni-Cr-Al catalyst at about 110° C. and under a hydrogen pressure of 230 to 280 bars.

The conversion of the analysis of the hydrogenated reaction product gave a yield of trimethylolpropane of 89.5% of theory.

EXAMPLE 3

2.5 g (0.012 mol) of copper-II acetate were dissolved in 2,500 g of an aqueous formaldehyde solution (about 30% by weight of formaldehyde, 25 mols). First 62.5 ml (0.45 mol) of triethylamine and then 62.5 g of a 20% strength by weight sodium hydroxide solution were added dropwise to the solution at 0° C. 180 g (2.5 mols) of n-butanal were then added dropwise to this solution in the course of half an hour at about 0° C. whilst stirring.

The mixture was subsequently left to stand for 5 hours at the same temperature, and 10.74 g of the solution were then acidified with acetic acid.

A solution of 1.9 g (0.032 mol) of dimethylaminoborane dissolved in 25 ml of methanol was added to this sample and the mixture was heated at the boil for one hour under reflux.

The reaction product hydrogenated in this manner was analysed and the analysis was converted for the total batch.

The yield was 94.5% of theory of trimethylolpropane, relative to the n-butanal employed.

EXAMPLE 4

A mixture of 1,000 g of aqueous formaldehyde solution (about 30% by weight of formaldehyde and 72 g of n-butanal) was cooled to about 0° C., 10 g (0.13 mol) of calcium hydroxide in powder form were introduced at this temperature, whilst stirring and cooling, and the mixture was then left to stand for 24 hours at about −4° C. to about 0° C.

10.425 g of the reaction mixture thus obtained were acidified with acetic acid and, after adding 1.9 g of trimethylaminoburane dissolved in 25 ml of methanol, the mixture was heated at the boil for one hour under reflux.

The sample was then analysed and the analysis was converted for the total batch. The yield was 88.% of theory of trimethylolpropane, relative to the n-butanal employed.

EXAMPLE 5

First 50 ml (0.36 mol) of triethylamine and then 144 g (2.0 mols) of n-butanal were added dropwise to a solution, cooled to about 0° C., of 2 g (0.01 mol) of copper-II acetate in 2,000 g of an aqueous formaldehyde solution (about 30% by weight of formaldehyde), whilst stirring and maintaining the temperature. The reaction mixture was then left to stand for 96 hours at about −2° C. to about 0° C.

Thereafter, a sample of 10.49 g was removed and acidified with acetic acid and, after adding 1.9 g of trimethylaminoborane dissolved in 25 ml of methanol, the mixture was heated at the boil for one hour under reflux.

Conversion of the analysis of this sample gave a yield of 74.6% of theory of trimethylolpropane, relative to the n-butanal employed.

EXAMPLE 6

5 g (0.03 mol) of manganese-II acetate, 125 ml (0.9 mol) of triethylamine and 125 g of a 20% strength sodium hydroxide solution were slowly added successively to 5,000 g of an aqueous formaldehyde solution (30% by weight of formaldehyde, 50 mols) at about 0° C., whilst cooling and whilst stirring. 360 g (5.0 mols) of n-butanal were then added dropwise at the same temperature in the course of half an hour, whilst stirring and cooling. The reaction mixture was then left to stand for 24 hours at temperatures between −2° C. and −8° C., and then neutralised at about −8° C. with acetic acid.

The reaction mixture was then evaporated in a Sambay evaporator under normal pressure under 760 mm Hg, most of the excess formaldehyde distilling off. The evaporation residue was 1,948 g.

61 g of this residue were diluted with 61 g of isopropanol and were hydrogenated in the presence of 15 g of a Ni-Cr-Al catalyst in an autoclave at about 110° C. and under a hydrogen pressure of 200 to 280 bars.

The analysis of the isolated product was converted for the total batch; the yield of trimethylolpropane was 88.% of theory, relative to the n-butanal employed.

EXAMPLE 7

50 g of 20% strength by weight sodium hydroxide solution were added dropwise to 2,000 g of an aqueous formaldehyde solution (30% by weight of formaldehyde) at 0° C., whilst stirring and cooling, and then 144 g of n-butanal were added dropwise in the course of 45 minutes, also at 0° C. The reaction mixture was left to stand for 24 hours at temperatures between 0° C. and −6° C.

The reaction mixture was then neutralised with acetic acid, and the solution was evaporated to 34.4% of its weight in a Sambay evaporator under 760 mm Hg. 130 g of the evaporation residue were then taken up in 500 ml of acetone, the acetone solution was filtered and the filtrate was evaporated in a rotary evaporator under a water-pump vacuum.

The resulting residue was diluted with water in the weight ratio 1:1 and hydrogenated in an autoclave in the presence of 15 g of a Ni-Cr-Al catalyst at about 110° C. and under a hydrogen pressure of 200 to 280 bars.

Conversion of the analysis gave a yield of 85.8% of theory of trimethylolpropane, relative to the n-butyraldehyde employed.

EXAMPLE 8

1 g (0.005 mol) of copper-II acetate was added to 2,000 g of an aqueous formaldehyde solution (about 30% by weight of formaldehyde), and 30 ml (0.22 mol) of triethylamine, 50 g of a 20% strength by weight sodium hydroxide solution and then 116 g (2.0 mols) of propanal were added dropwise successively to the solution, cooled to 0° C., at this temperature, whilst stirring and cooling. The reaction mixture was then kept for 24 hours at temperatures between about −1° C. and −5° C. and was then evaporated to 38% of its weight in a Sambay evaporator.

150 g of this evaporation residue were taken up in 600 ml of acetone, the acetone solution was filtered and the filtrate was concentrated further in a rotary evaporator under a water-pump vacuum.

The resulting residue was diluted with water in the weight ratio 1:1 and was hydrogenated in an autoclave in the presence of 15 g of a Ni-Cr-Al catalyst at about 110° C. and under a hydrogen pressure of 200 to 280 bars.

Conversion of the analysis of the hydrogenation mixture gave a yield of 81.4% of theory of trimethylolethane, relative to the propanal employed.

EXAMPLES 9 TO 15

In Examples 9 to 15 which follow, the particular amounts indicated of one or more bases were added to the particular amount indicated of aqueous formaldehyde solution (about 30% by weight of formaldehyde) at 0° C. and the amount indicated of n-butanal was added dropwise to this mixture, also at 0° C. whilst stirring, in the course of about half an hour, and the reaction mixture was then left to stand for 6 hours at about 0° C.

Thereafter, a sample of about 10 g of the reaction mixture was acidified with acetic acid, and 1.9 g of dimethylaminoborane dissolved in 25 ml of methanol were added. Thereafter, the mixture was heated at the boil for one hour under reflux and then analysed.

In Table I which follows, tbe nature and amount of the bases used and the yields of trimethylolpropane (TMP) in % of theory, found by converting the analyses to the total batch, are indicated for each example.

Table I

| Example | Butyraldehyde (mols) | Formalin (30% strength) (mols of formaldehyde) | Base [g] | Time [hours] | TMP [%] | C$_5$-diol [%] |
|---|---|---|---|---|---|---|
| 9 | 1 | 1,000 (10) | NaOH, 5 triethylamine, 17 | 6 | 81.5 | — |
| 10 | 1 | 1,000 (10) | Ca(OH)$_2$, 10 | 6 | 78.6 | — |
| 11 | 1 | 1,000 (10) | NaOH, 5 triethylamine, 18 Cd acetate, 1 | 6 | 89.9 | — |
| 12 | 1 | 1,000 (10) | NaOH, 5 triethylamine, 18 Cu acetate, 1 | 6 | 92 | — |
| 13* | 1 | 230 (2.3) | NaOH, 4.3 | 6 | 57.6 | 1.5 |
| 14* | 1 | 230 (2.3) | NaOH, 4.2 | 6 | 57.1 | 4.5 |
| 15* | 1 | 230 (2.3) 770 g of H$_2$O | Ca(OH)$_2$, 10 | 20 | 55 | — |

*Examples 13 to 15 are comparison examples

What is claimed is:

1. A process for the preparation of a trimethylolalkane of the formula

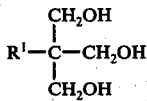  (I)

wherein

R$^1$ represents an aliphatic radical which comprises contacting an aldehyde of the formula

  (II)

wherein

R$^1$ has the meaning indicated above with formaldehyde employing a mol ratio of formaldehyde to aldehyde of at least 8:1 in the presence of an aldol condensation base at a temperature between −20° and 5° C. and thereafter hydrogenating the resultant 2,2-dimethylolalkanal.

2. A process according to claim 1 wherein the reaction of the aldehyde with formaldehyde is carried out in the presence of an ion of an element selected from the group consisting of cobalt, nickel, copper, manganese, zinc, silver, and cadmium.

3. A process according to claim 2 wherein the ion is present in an amount of 0.001 to 0.03 gram atom per mol of aldehyd of the formula II.

4. A process according to claim 1 wherein the base is present in an amount of 0.01 to 0.3 mol per mol of aldehyde.

5. A process according to claim 1 wherein the reaction of the formaldehyde with the aldehyde is carried out at a pH of 9 to 12.

6. A process according to claim 1 wherein R$^1$ is a straight chain or branched alkyl radical having up to 12 carbon atoms which can optionally be substituted by an alkyl or alkoxy group having 1 to 3 carbon atoms in the chain.

7. A process according to claim 1 wherein the aldehyde-formaldehyde reaction is carried out in the presence of an ion of an element of group VII and/or VIII and/or sub-group I and/or sub-group II of the Period System of the Elements.

* * * * *